United States Patent [19]
Lee

[11] Patent Number: 6,135,948
[45] Date of Patent: Oct. 24, 2000

[54] CONVERTIBLE LARYNGOSCOPE

[76] Inventor: Han Shik Lee, 134 The Dell, Searingtown, N.Y. 11507

[21] Appl. No.: 09/237,096

[22] Filed: Jan. 25, 1999

[51] Int. Cl.[7] .................................................. A61B 1/267
[52] U.S. Cl. ........................................... 600/189; 600/131
[58] Field of Search .................................... 600/113, 173, 600/175, 185, 188, 189; 433/29, 30, 31

[56] References Cited

U.S. PATENT DOCUMENTS

| | | | |
|---|---|---|---|
| 1,945,380 | 1/1934 | Russell | 600/189 |
| 3,643,654 | 2/1972 | Felbarg | 600/189 |
| 3,870,037 | 3/1975 | Cadariu et al. | 600/189 |
| 3,884,222 | 5/1975 | Moore | 600/188 |
| 4,090,506 | 5/1978 | Pilgrim | 433/31 |
| 4,212,105 | 7/1980 | Hukuba | 433/30 |
| 4,629,425 | 12/1986 | Detsch | 433/31 |
| 4,760,840 | 8/1988 | Fournier, Jr. et al. | 606/15 |
| 4,915,626 | 4/1990 | Lemmey | 433/31 |
| 5,027,138 | 6/1991 | Gandrud | 348/66 |
| 5,261,392 | 11/1993 | Wu . | |
| 5,348,470 | 9/1994 | McGowan et al. | 433/30 |
| 5,349,943 | 9/1994 | Ruiz . | |
| 5,406,941 | 4/1995 | Roberts . | |
| 5,584,795 | 12/1996 | Valenti . | |

*Primary Examiner*—John P. Leubecker
*Attorney, Agent, or Firm*—Michael I Kroll

[57] ABSTRACT

A convertible laryngoscope includes a deployable integral mirror to allow the doctor to clearly view the larynx and more easily insert an endotracheal tube. In many patients, due to injury, deformation, or an existing medical condition, the introduction of the endotracheal tube can be a prolonged and difficult affair, the doctor being forced to work blind when they cannot gain an unobstructed view of the larynx and the path that the cannula or tube needs to travel during intubation. The present invention addresses this problem by providing the above mentioned mirror, which is disposed in a first position proximate the laryngoscope blade during the initial introduction of the blade into the patient's mouth. Once the base of the tongue is reached and depressed, the user may deploy the mirror into a second position extending towards the soft palate that allows a reflected view towards the larynx and epiglottis. This allows the person intubating the patient to clearly see the path that the cannula needs to take, preventing inadvertent damage to the soft tissue of the mouth and throat. A fixed integral light source is included that is directed towards the deployed mirror position to illuminate the proposed path.

9 Claims, 15 Drawing Sheets

FIG 1

( PRIOR ART )

FIG 16

CONVERTIBLE LARYNGOSCOPE

BACKGROUND OF THE INVENTION

1. Field of the Invention

The present invention relates generally to direct laryngoscopes, and more specifically, to a laryngoscope having means for extending a mirror away from the blade in small selectable increments wherein the extending means locks into said small increments and having means for adjusting the mirror in small selectable increments while in its extended state wherein the adjusting means locks.

2. Description of the Prior Art

There are other laryngoscopes designed to aid in intubation. Typical of these is U.S. Pat. No. 5,584,795 issued to Valenti on Dec. 17, 1996.

Another patent was issued to Wu on Nov. 16, 1993 as U.S. Pat. No. 5,261,392. Yet another U.S. Pat. No. 5,349,943 was issued to Ruiz on Sep. 27, 1994 and still yet another was issued on Apr. 18, 1995 to Roberts as U.S. Pat. No. 5,406,941. These patents will be discussed in detail further below.

U.S. Pat. No. 5,584,795 to Valenti disclose a Pivoting laryngoscope with a power driven spatula for performing intubation in patients. The laryngoscope includes a handle for gripping the laryngoscope, and a curved spatula blade having one end connected to the handle. The spatula blade is subdivided into a plurality of adjacent, sequentially arranged sections. At least two of the sections are pivotally connected together at a fulcrum. A motor assembly is located within the handle and is activated for generating movement of the pivoted, interconnected sections. A motion transmission assembly operatively connects the motor assembly to the section, whereby the section is moved relative to the fulcrum and within a predetermined arc, thereby changing a curvature of the curved spatula blade.

U.S. Pat. No. 5,261,392 to Tzu-Lang Wu discloses a laryngoscope comprised of an integral handle and curved blade with a bivalve element to form an enclosed passageway with the curved blade, the handle shaped to receive a fiberoptic bundle assembly and the interior of the curved blade having a channel into which a fiberoptic bundle assembly may be placed, with the distal end of said channel forming a circumference for containing the distal end of the fiberoptic bundle assembly.

U.S. Pat. No. 5,349,943 to Ruiz discloses a mirror laryngoscope blade which includes a curved shaft, a mount on a proximal end of the shaft for attaching the blade to a handle, and a flange extending from an edge of the shaft. The mirror includes a primary viewing surface and a tip inclined toward the shaft. The tip is located between the distal end and the distal quarter point of the shaft.

U.S. Pat. No. 5,406,941 discloses a laryngoscope for use in endotracheal intubation wherein the blade is adjustable between a straight surface and a curved surface by a rotatable camming member fixedly attached to the blade by a pair of straps.

While these laryngoscopes may be suitable for the purposes for which they were designed, they would not be as suitable for the purposes of the present invention, as hereinafter described.

SUMMARY OF THE PRESENT INVENTION

The present invention is an improved convertible laryngoscope that includes a deployable integral mirror to allow the doctor to clearly view the larynx and more easily insert an endotracheal tube. In many patients, due to injury, deformation, or an existing medical condition, the introduction of the endotracheal tube can be a prolonged and difficult affair, the doctor being forced to work blind when they cannot gain an unobstructed view of the larynx and the path that the cannula or tube needs to travel during intubation. The present invention addresses this problem by providing the above mentioned mirror, which is disposed in a first position proximate the laryngoscope blade during the initial introduction of the blade into the patient's mouth. Once the base of the tongue is reached and depressed, the user may deploy the mirror into a second position extending towards the soft palate that allows a reflected view towards the larynx and epiglottis. This allows the person intubating the patient to clearly see the path that the cannula needs to take, preventing inadvertent damage to the soft tissue of the mouth and throat. A fixed integral light source is included that is directed towards the deployed mirror position to illuminate the proposed path.

Thus. a primary object of the present invention is to provide a laryngoscope which can be utilized as a direct laryngoscope or as an indirect laryngoscope.

Another object of the present invention is to provide a laryngoscope having a mirror which can be extended away from the blade.

Yet another object of the present invention is to provide a laryngoscope having a mirror which can be adjusted after it has been extended away from the blade.

Still yet another object of the present invention is to provide a laryngoscope having a light which can be used in either the direct or indirect mode.

Additional objects of the present invention will appear as the description proceeds.

The present invention overcomes the shortcomings of the prior art by providing a laryngoscope having means for extending a mirror away from the blade in small selectable increments wherein the extending means locks in these small increments and further having means for adjusting the extended or deployed mirror in small selectable increments while in its extended state, and where this extended adjusting means also may be locked into the desired position.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Turning now descriptively to the drawings, in which similar reference characters denote similar elements throughout the several views, the Figures illustrate the convertible laryngoscope of the present invention.

DETAILED DESCRIPTION OF THE PREFERRED EMBODIMENTS

Turning now descriptively to the drawings, in which similar reference characters denote similar elements throughout the several views, FIGS. 1 through 16 illustrate both the prior art and the novel convertible laryngoscope of the present invention in both its contemplated embodiments.

Figure 1:
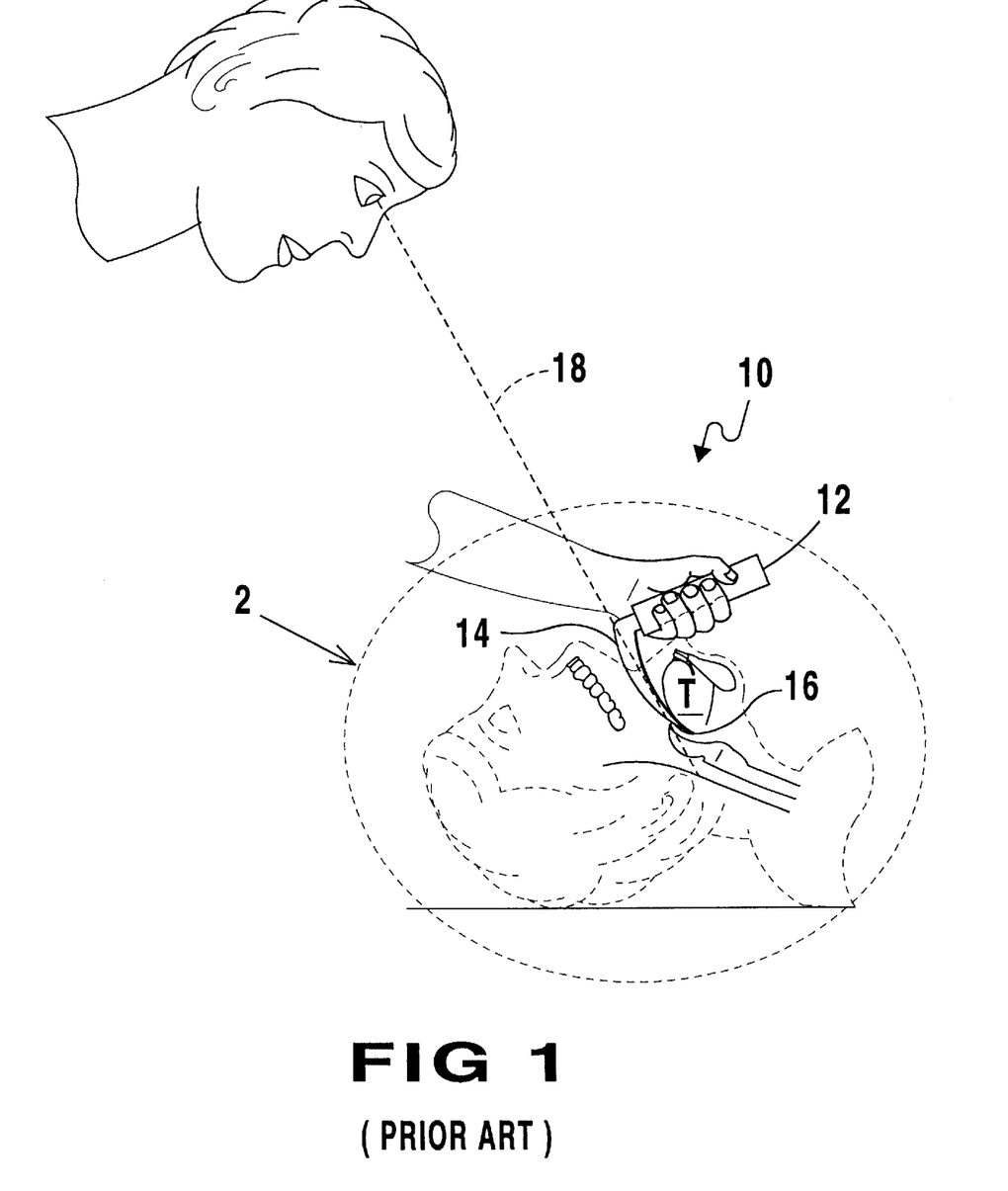
FIG. 1 is a diagrammatic view of a direct laryngoscope where, because of any number of conditions, the vocal cords cannot be viewed and where it is desired when performing the intubation that the vocal cords should be visible to the doctor.
Figure 2:
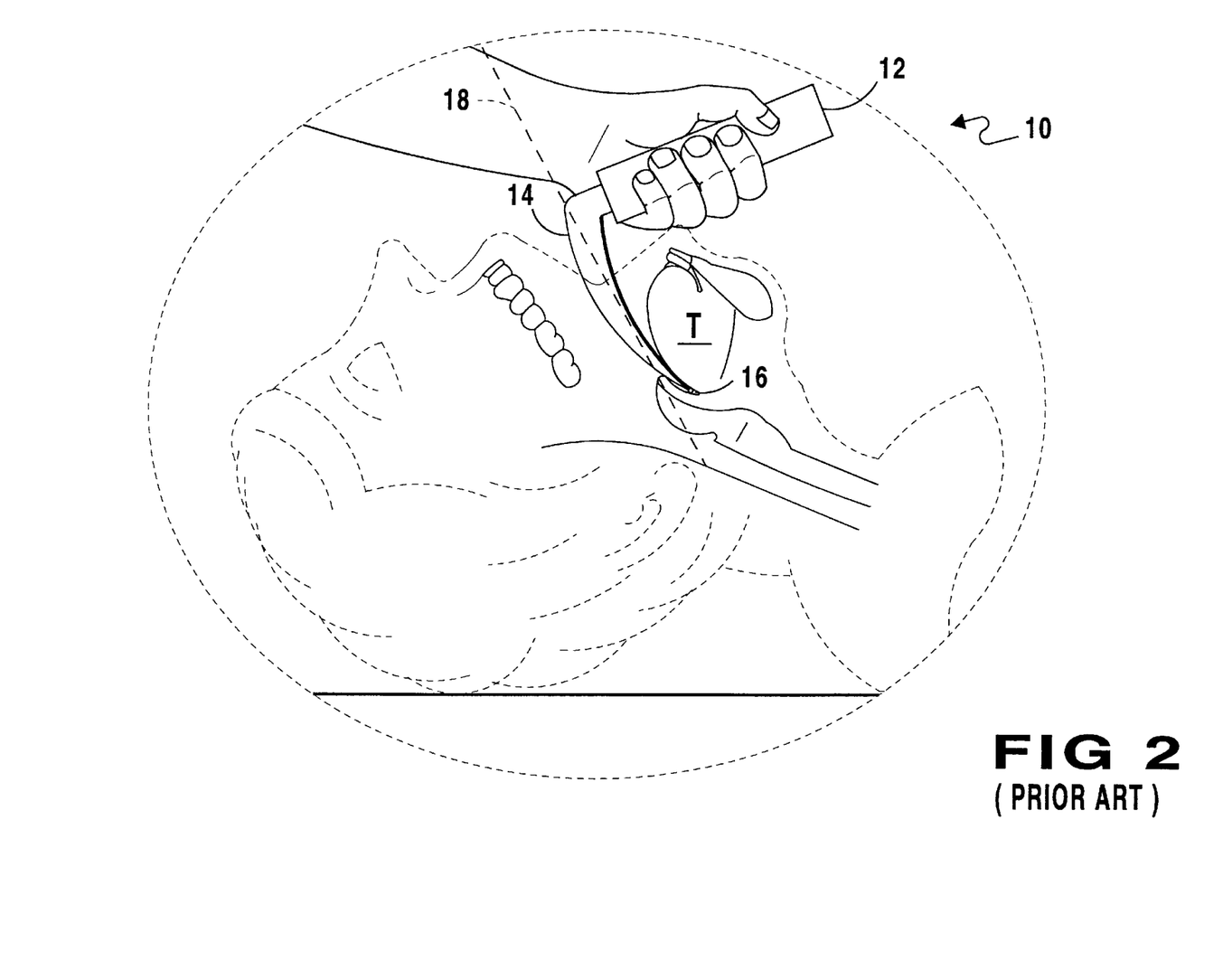
FIG. 2 is an enlarged view, taken from FIG. 1 as indicated, of the direct laryngoscope where, because of any number of conditions, the vocal cords cannot be viewed and where it is desired when performing the intubation that the vocal cords should be visible to the doctor.

In FIGS. 1 and 2, a prior art laryngoscope is seen in use and is generally indicated at 10. Using the handle 12, the blade 14 is inserted into the patient's mouth until the terminus 16 of the blade 14 is located proximate the base of the patient's tongue T. A drawback of this, existing laryngoscope 10, is that the line of sight of the physician, as indicated by the broken line 18 may not reach sufficiently far down into the patient's throat to allow for the easy introduction of the endotracheal tube. This leads to the doctor having to work by feel, possibly leading to damage of the soft tissue of the mouth or the teeth of the patient.

Figure 3:
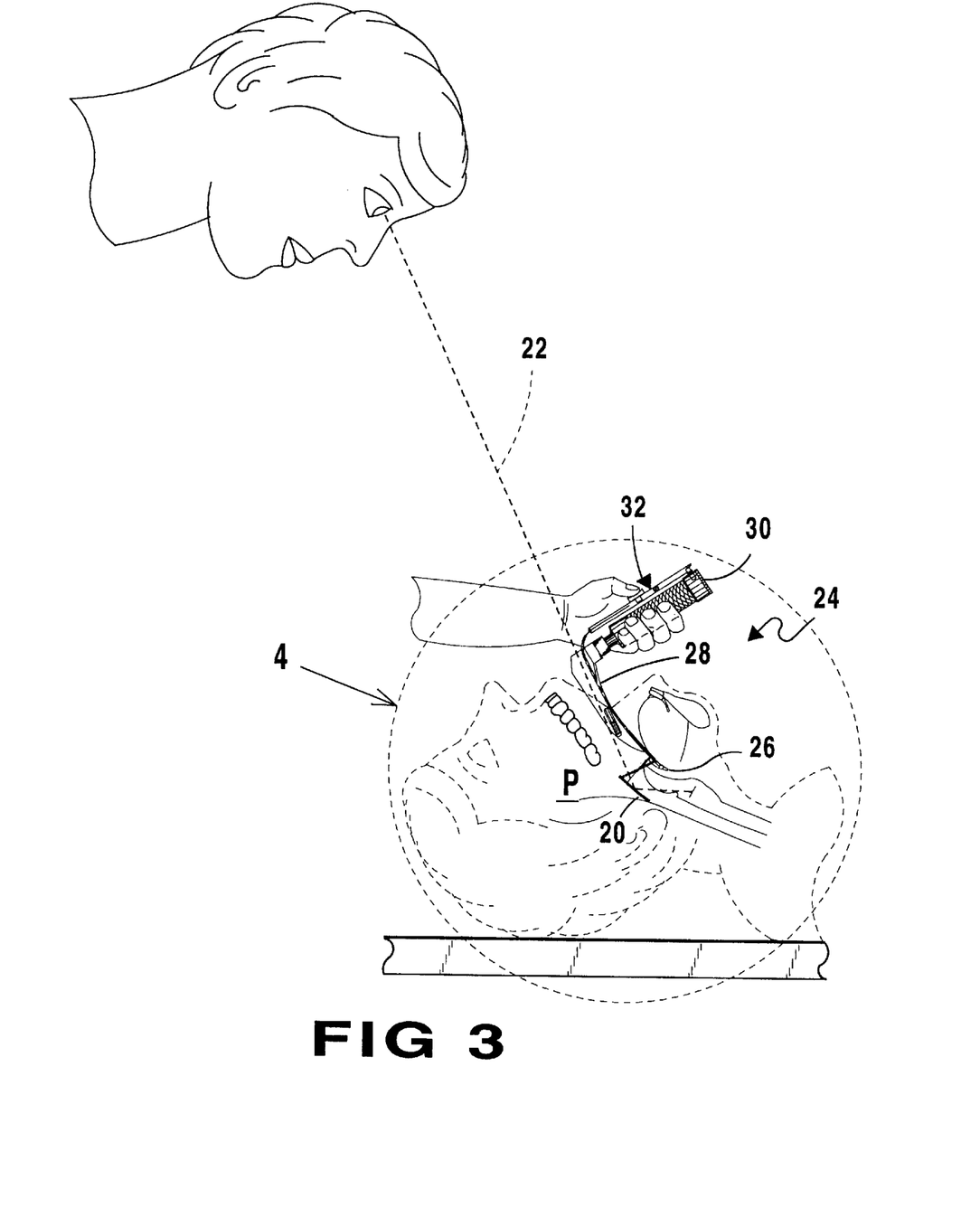
FIG. 3 is a diagrammatic view of the present invention wherein the mirror of the laryngoscope has been extended and the angle adjusted to view the vocal cords.
Figure 4:
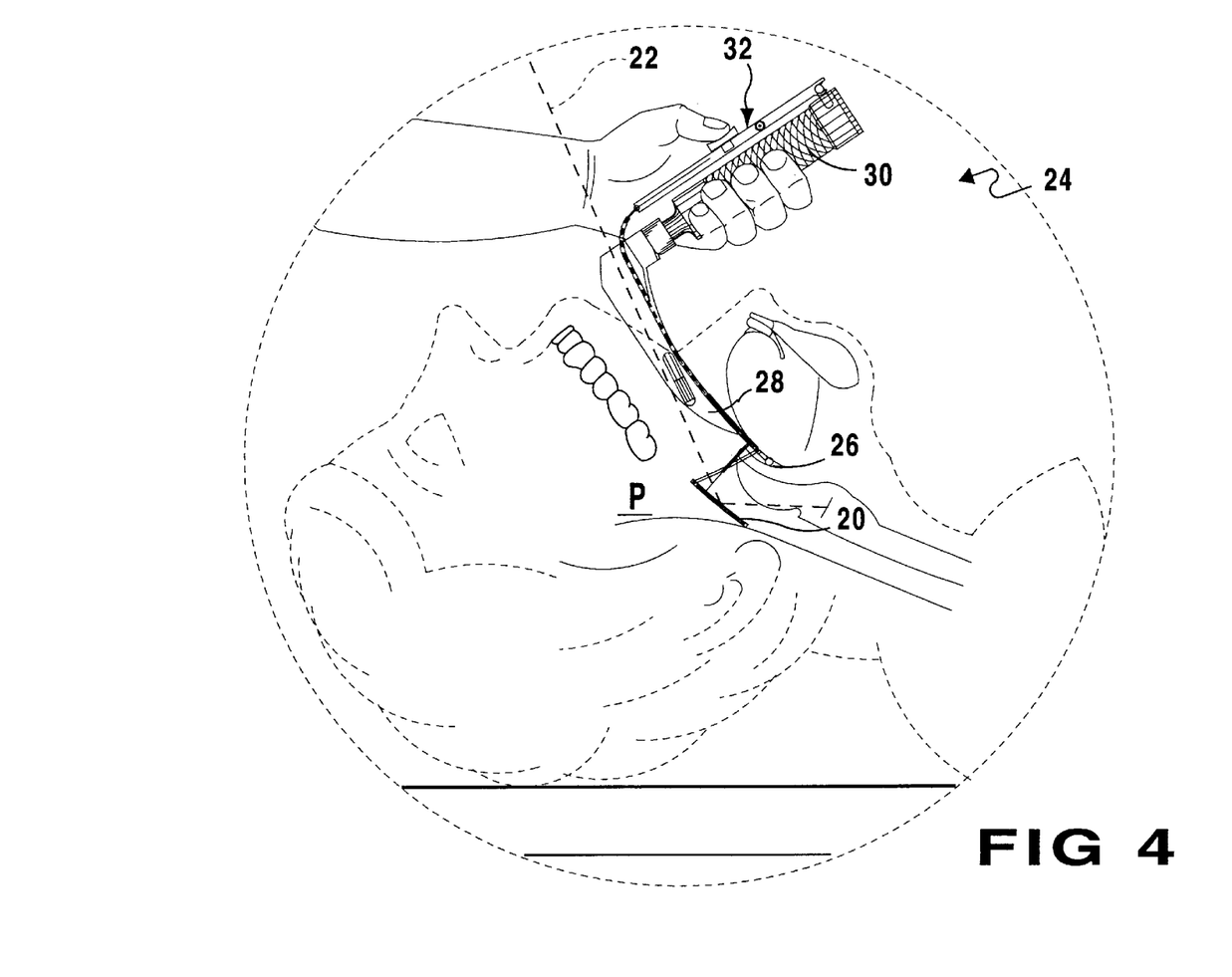
FIG. 4 is an enlarged view, taken from FIG. 3 as indicated, showing the present invention wherein the mirror of the laryngoscope has been extended and the angle adjusted to view the vocal cords.

Turning now to FIGS. 3 and 4, the improved laryngoscope of the present invention, denoted as 24 is seen in use with the deployable mirror 20 of the device extended towards the soft palate P of the patient. With the deployable mirror 20 extended in this way, the line of sight of the physician attempting the intubation of the patient is indicated by the dotted line 22.

Figure 5:
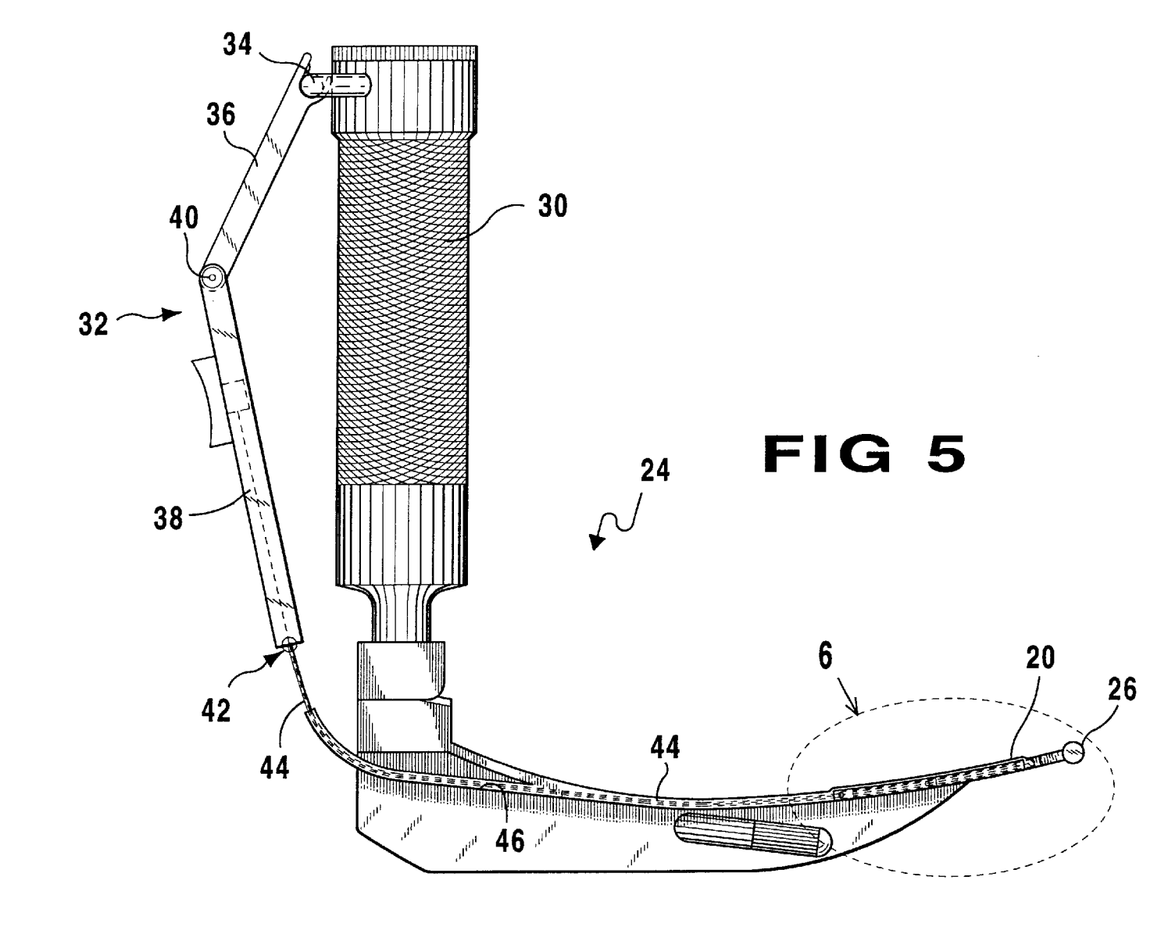
FIG. 5 is a side view of the preferred embodiment of the present invention. Shown is a handle with an attached blade. The blade has a hollow portion for the mirror extension means and for the mirror adjustment means.

For the best understanding of the operation of the present invention, turn to FIG. 5, which shows the improved convertible laryngoscope generally indicated at 24. In this Figure, the deployable mirror 20 is in place disposed proximate the terminus 26 of the blade 28 of the instant invention 24. Attached to the blade is a handle 30, opposite the terminus 26, this handle being similar to the handles seen in the prior art. In the present invention, however, a second, depressible pivoting handle or grip 32 is provided. It attaches to handle 30 at top pivot point 34. Pivoting handle 32 has two sections. A first upper section 36 and a lower section 38. These two sections 36 and 38 are attached at central pivot 40. Extending from the bottom 42 of lower handle section 38 are control cables 44. These will be discussed in further detail below. The control cables 44 extend through the blade 28 by means of the control cable aperture or bore 46. It should be understood, that as in the prior art, the size of the blade 28 varies with the size of the patient and a wide variety of these blade sizes would be available to the practitioner. In all cases, the control cable bore or aperture 46 would be located in a analogous position.

Figure 6:
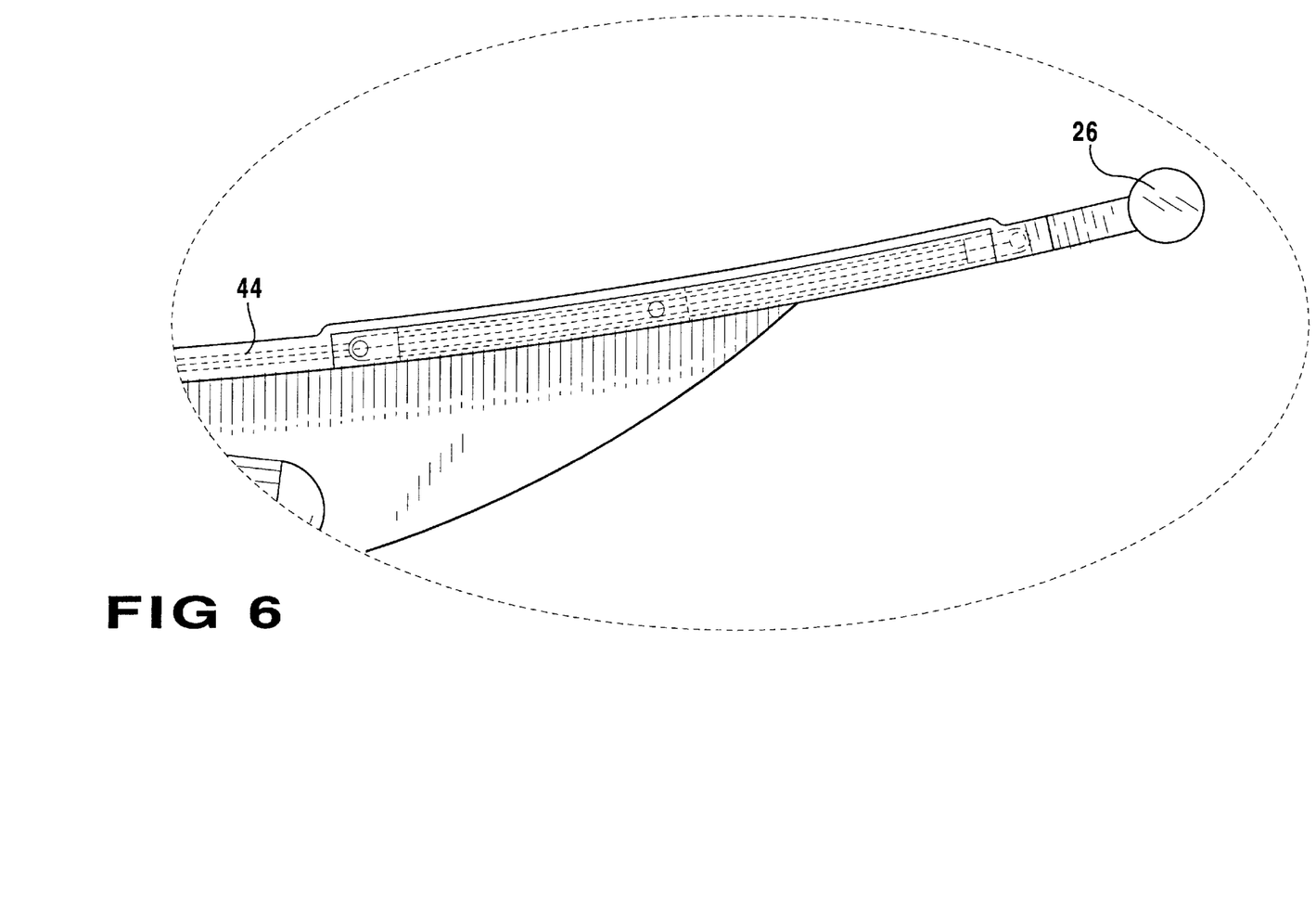
FIG. 6 is an enlarged view of the preferred embodiment, taken from FIG. 5 as indicated, showing the mirror in the closed position.
Figure 7:
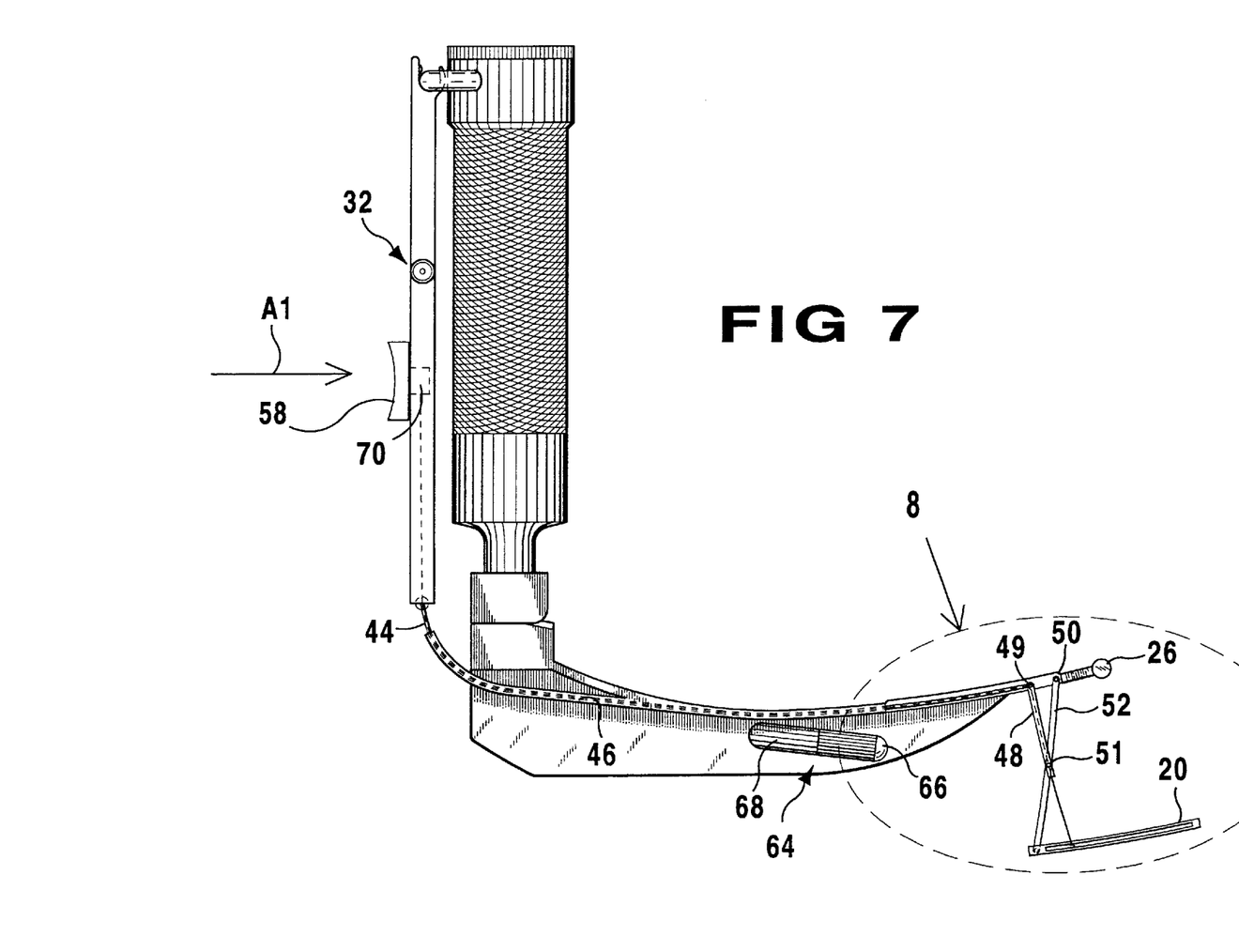
FIG. 7 is a side view of the preferred embodiment showing the mirror in the extended position, accomplished by moving the pivotal handle toward the body of the apparatus.
Figure 8:
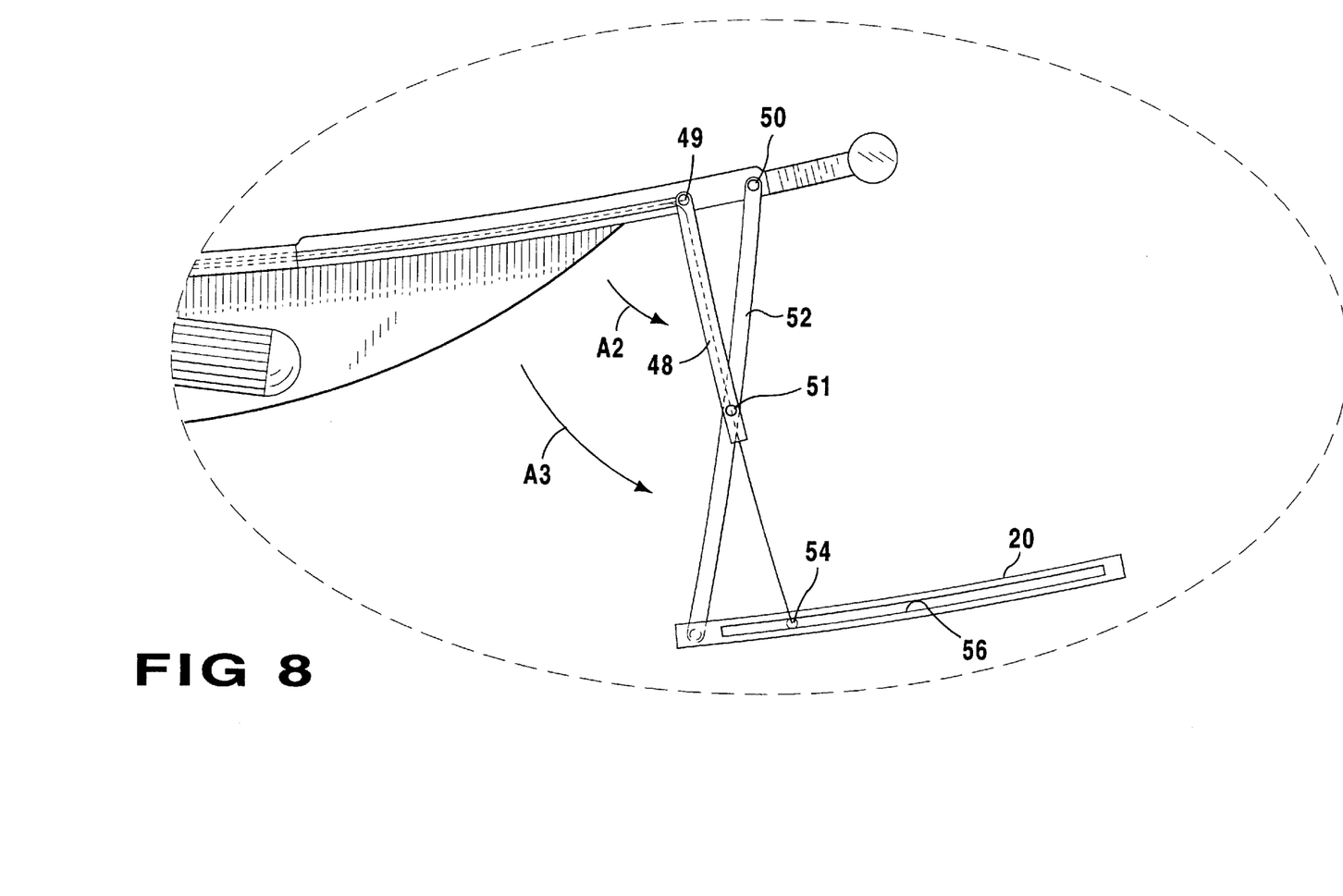
FIG. 8 is an enlarged view of the preferred embodiment, taken from FIG. 7 as indicated, showing the mirror in the extended position, this being accomplished by moving the pivotal handle toward the body of the apparatus.
Figure 9:
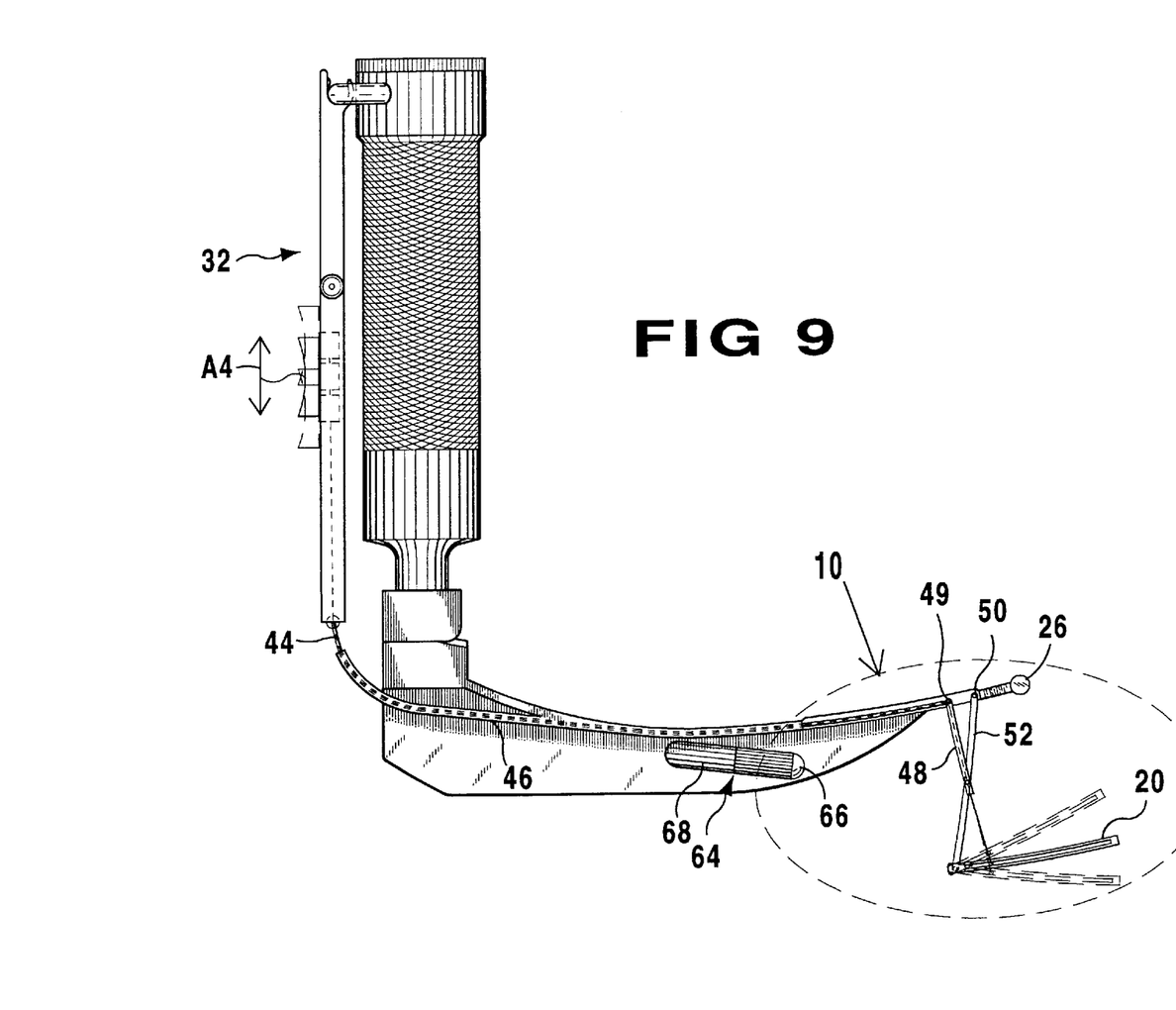
FIG. 9 is a side elevation of the preferred embodiment of the present invention showing the alternate locations of the mirror and means for adjusting the mirror by sliding the lever located under the thumb.

Turning now to FIGS. 6–8, the deployment of the mirror will be discussed. In FIG. 7, when the pivoting handle or grip 32 is moved in the direction of the directional arrow A1, the control cables are urged through control cable aperture 46 to move the various pivoting arms into approximately the positions that are seen in FIGS. 7 and 8. The first pivot arm 48 swings out in the direction indicated by directional arrow A2, hinging off of first pivot point 49. Due to the second deploying pivot point 50, and the intersecting pivot point 51 that cooperates between them, second pivot arm 52 swings out in the direction indicated by directional arrow A3. This carries the deployable mirror 20 into the desired position in the patient's throat. Control cable 44 terminates in a sliding member 54 that rides within a sliding slot 56 that runs along or within the side of deployable mirror 20.

Figure 10:
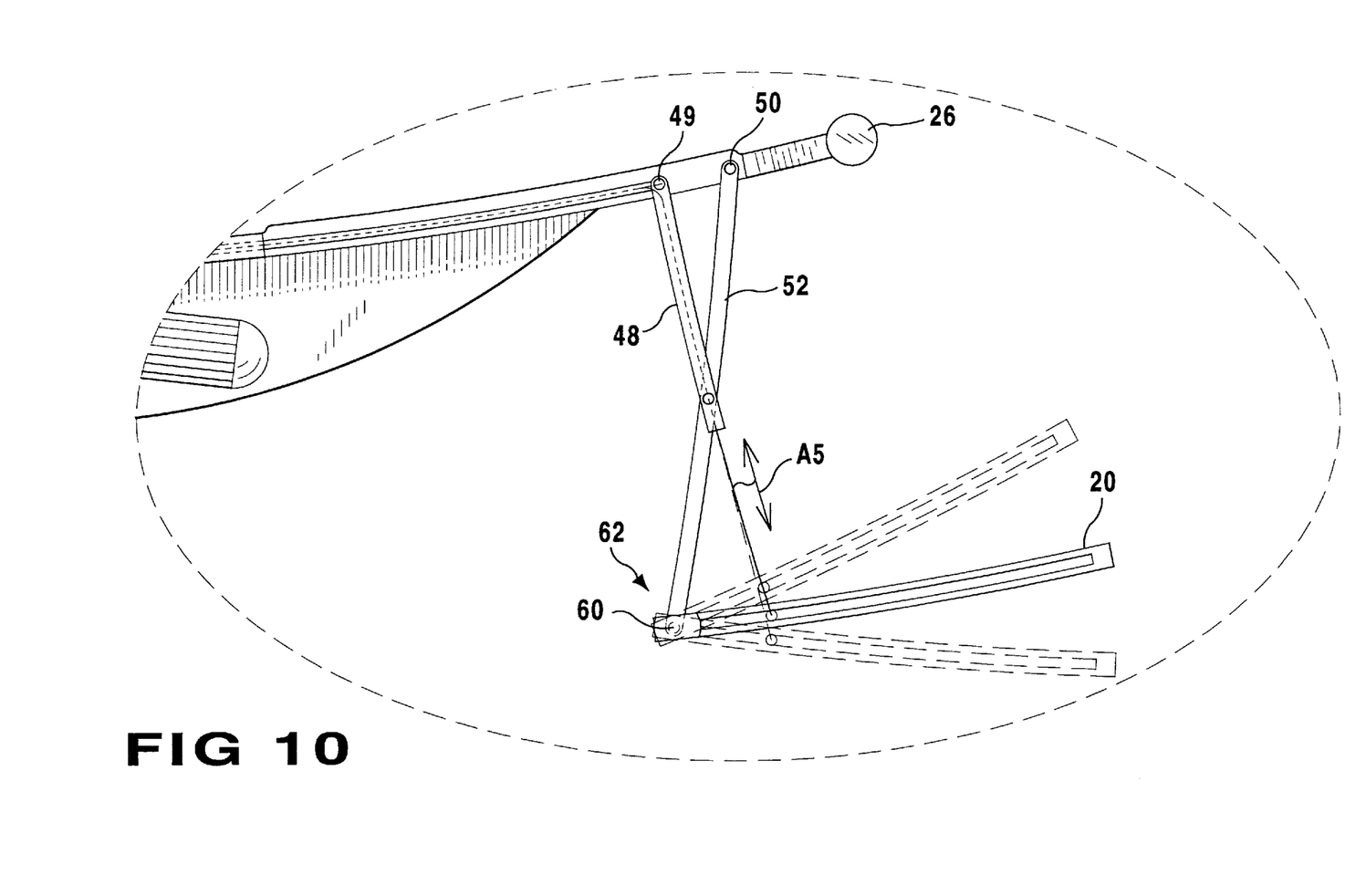
FIG. 10 is an enlarged view of the preferred embodiment of the present invention, taken from FIG. 9 as indicated, showing the alternate locations of the mirror and means for adjusting the mirror by sliding the lever located under the thumb.

The sliding member 54 and its slot 56 allow for the fine adjustment of the deployable mirror into whatever angle is needed by the intubating technician or physician. This adjustment is clearly shown in FIGS. 9 and 10. By moving the mirror angle adjustment knob 58 along the direction indicated by the arrow A4, the angle of the deployable mirror 20 with regard to the angle of the blade 20, as it is held at the base of the tongue, can be altered. As is seen in FIG. 10, the control cable 44, moving along the direction indicated by directional arrow A5 urges the deployable mirror 20 about mirror pivot point 60 located at the terminal end 62 of the second pivot arm 52. It should be emphasized that it is necessary for the operation of the instant invention that the material that makes up the control cable 44 be of sufficient stiffness to permit the rotation of the first and second pivot arms 48, 52 around their respective pivot points 49 and 50.

Located within or alongside the blade 20 of the present invention is a light source indicated in the various Figures at 64. The light source includes a light emitting portion 66, that could be either a bulb or LED source and a power means 68. Various types of power sources could be used, such as regular batteries, rechargeable type batteries, or even an external power supply (not shown). This light source 64, in combination with the pivoting deployable mirror 20, allows the person performing the intubation to direct the illumination at the desired area within the patient's throat, as is illustrated in FIGS. 3 and 4.

Figure 11:
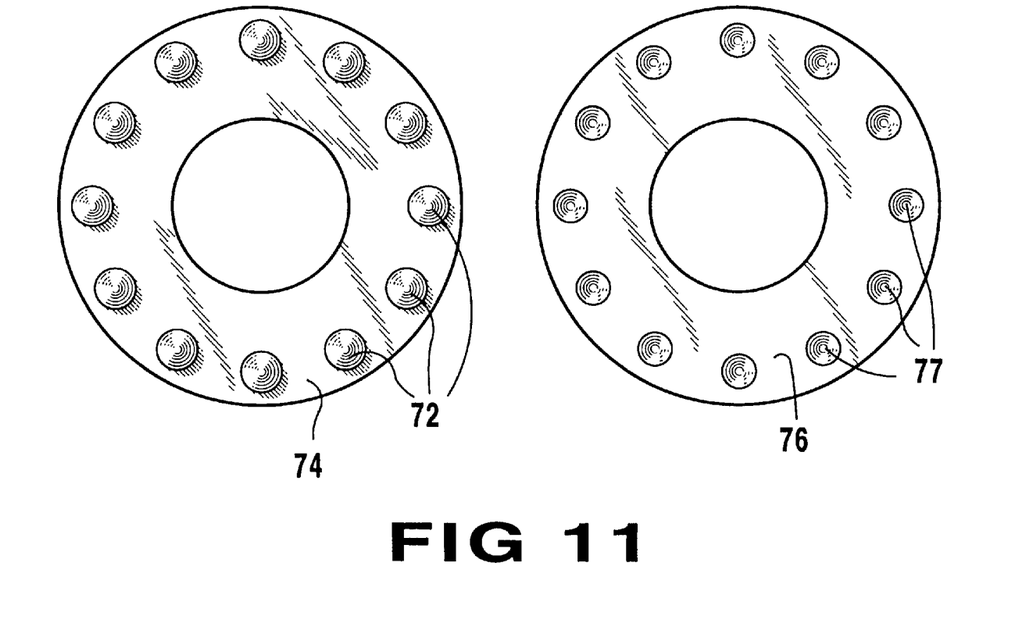
FIG. 11 is a top plan view of the locking mechanism of the present invention wherein one surface has a number of depressible ball bearings under spring pressure and the other surface has a plurality of mating holes wherein the first can be rotated as needed and lock when balls are seated in the holes.
Figure 12:
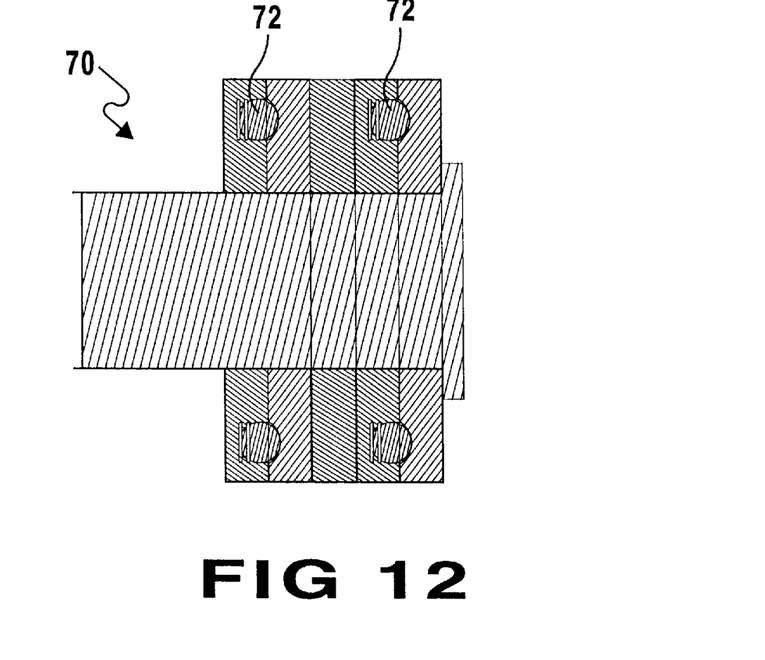
FIG. 12 is a cross sectional view of the locking mechanism.
Figure 13:
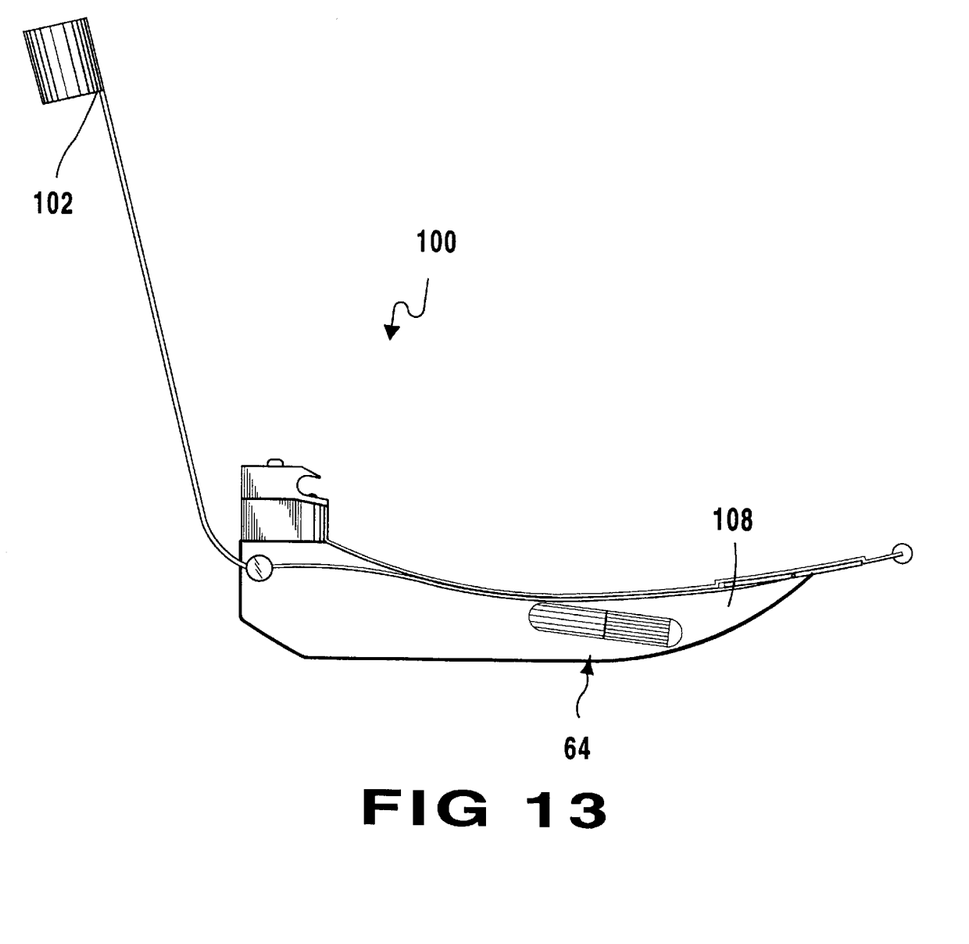
FIG. 13 is a side elevation of an alternate embodiment of the present invention showing the blade assembly which will be attached to the conventional handle in the conventional manner.
Figure 14:
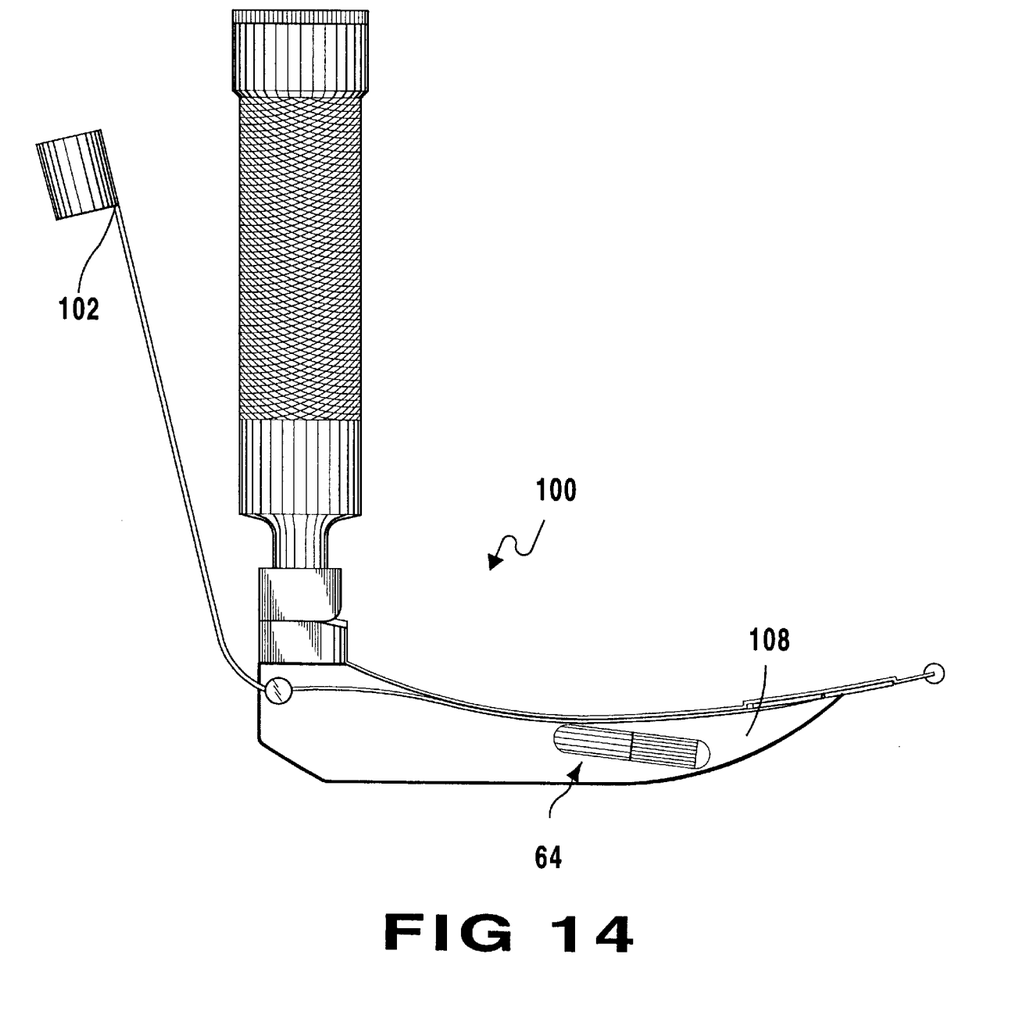
FIG. 14 is a side elevation of the alternate embodiment of the present invention showing the blade assembly attached to the handle in the operative condition.

Turning now to FIGS. 11 and 12, the locking mechanism for holding the deployable mirror 20 into its desired position will be discussed. In the embodiment described herein, the locking mechanism 70 is located proximate the mirror angle adjustment knob 58. Locking mechanism 70 consists of a series of biased ball detents 72 located about a first generally circular locking plate 74. Mating with this plate 74 is a second locking plate 76 that is provided with a plurality of matching ball detent recesses 77 that allow the biased ball detents to snap in and out of place when the various plates 74, 76 are rotated in relation one another. In a first position, the various plates are free to move in relation to one another, allowing the mirror angle adjustment knob 58 to be moved in the directions indicated by directional arrow A4 in FIG. 9. When the desired angle is reached, the operator can rotate the mirror angle adjustment rod, to snap the ball detents into place and lock the position of the sliding member 54 within the sliding slot 56 of the deployable mirror 20. Thus the deployable pivoting mirror 20 can be locked into the necessary position for a clear view of a specific patient's larynx for the intubation process.

Additionally, this locking mechanism could be used at the central pivot 40 of the pivoting handle 32 to allow for incremental deployment of the mirror 20 by alternatively engaging and disengaging the ball detents 72 within the various respective recesses 77.

Figure 15:
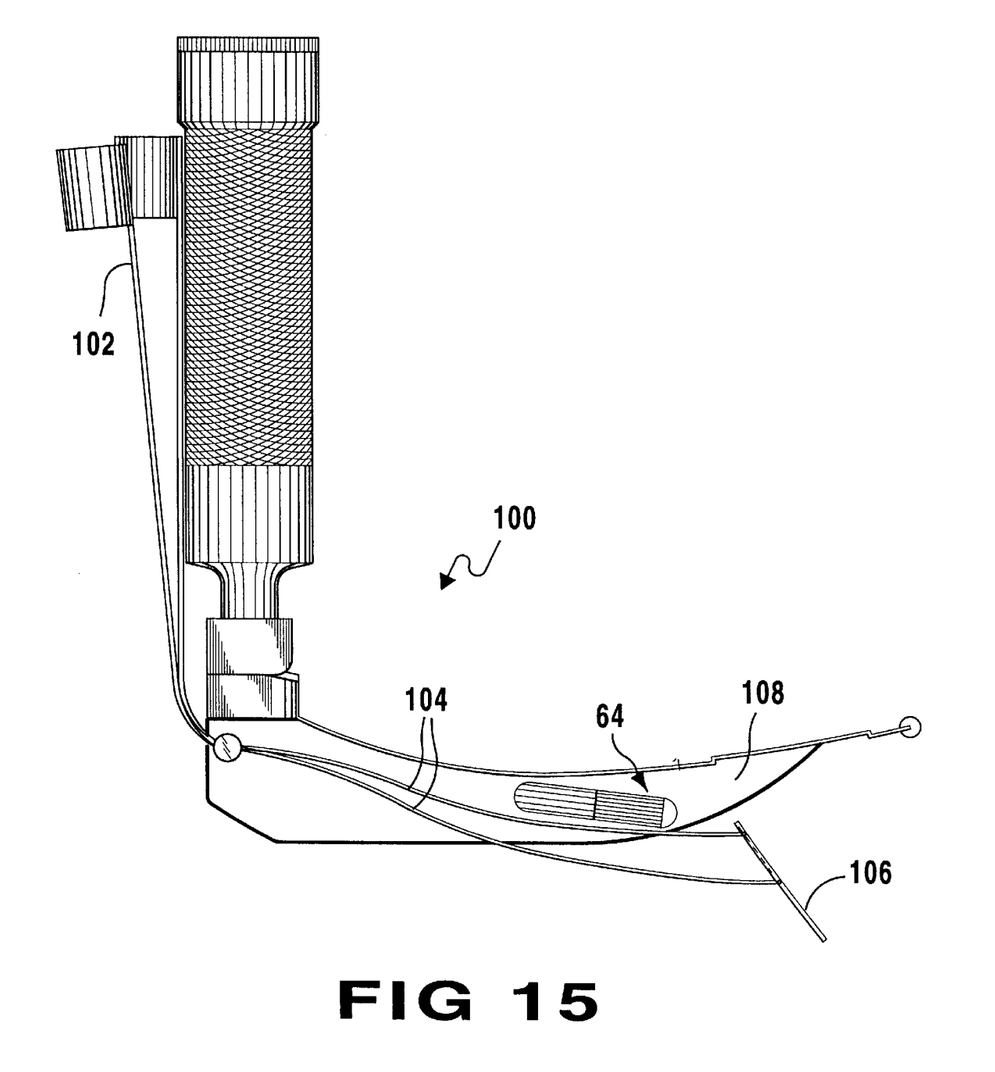
FIG. 15 is a side elevation of the alternate embodiment of the present invention showing the means for extending the mirror of the laryngoscope by depressing the lever located under the thumb.
Figure 16:
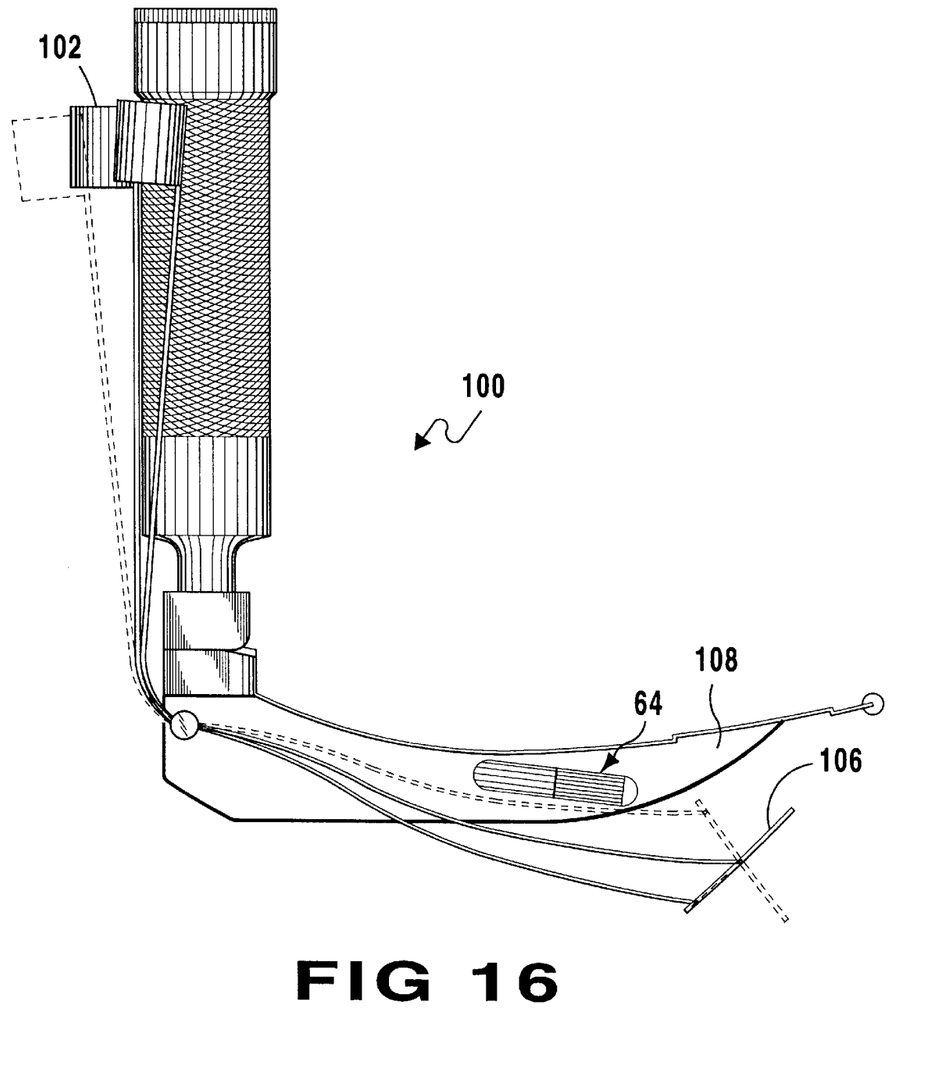
FIG. 16 is a side elevation of the present invention showing the means for adjusting the mirror of the laryngoscope by sliding the lever located under the thumb.

A second embodiment of the present invention is seen in FIGS. 13–16 and is generally indicated at 100. In this embodiment, the pivoting handle or grip is replaced by a lever 102 located proximate the thumb of the person performing the intubation. Note that the light source 64 is substantially identical to that of the first embodiment of the invention. Referring to FIG. 15, when the lever 102 is pressed as seen in the Figure, the control cable 104 deploys the mirror 106 into the position away from the blade 108. By sliding the lever as seen in FIG. 16, the mirror 106 can be pivoted as desired, resulting in the same direction of both the light and practitioner's view towards the desired area within the patient's throat.

What is claimed is:

1. A convertible laryngoscope for aiding in the view of a patient's throat while intubation is being performed, comprising:

a) a handle;

b) a laryngoscope blade removably detachable from said handle;

c) a mirror integral with and proximate to a terminus of said blade and moveable with respect to said blade, said mirror including manual deployment means for deploying said mirror in a fixed and controlled relationship with said blade whereby said laryngoscope blade is inserted into the mouth and throat of a patient, and said mirror is deployed through said manual deployment means into a fixed, controlled relationship with said blade such that a line of sight is maintained between a person performing an intubation and the throat of the patient;

d) said manual deployment means including a cable passing through a control cable aperture within said laryngoscope blade, said cable being pivotally attached to said mirror; and e) said manual deployment means further includes a depressible handle integral with said cable for deploying said mirror in a fixed and controlled relationship with said blade.

2. The convertible laryngoscope according to claim 1, wherein said manual deployment means further includes a first and a second pivot point proximate to, and integral with, said terminus of said laryngoscope blade, and where said first said second pivot points cooperate to extend said mirror when said cable is moved linearly within said control cable aperture.

3. The convertible laryngoscope according to claim 2, wherein said manual deployment means further includes a first pivot arm pivotally attached to said first pivot point and a second pivot arm pivotally attached to said second pivot point, said first and said second pivot arms sharing an intersecting pivot point.

4. A convertible laryngoscope for aiding in the view of a patient's throat while intubation is being performed, comprising:

a) a handle;

b) a laryngoscope blade removably detachable from said handle;

c) a mirror integral with and proximate to a terminus of said blade and moveable with respect to said blade, said mirror including manual deployment means for deploying said mirror in a fixed and controlled relationship with said blade, said manual deployment means including a cable passing through a control cable aperture within said laryngoscope blade, said cable being pivotally attached to said mirror whereby said laryngoscope blade is inserted into the mouth and throat of a patient, and said mirror is deployed through said manual deployment means into a fixed, controlled relationship with said blade such that a line of sight is maintained between a person performing an intubation and the throat of the patient; and d) said manual deployment means further includes a depressible handle integral with said cable for deploying said mirror in a fixed and controlled relationship with said blade.

5. The convertible laryngoscope according to claim 4, wherein said manual deployment means further includes a first and a second pivot point proximate to, and integral with, said terminus of said laryngoscope blade, and where said first said second pivot points cooperate to extend said mirror when said cable is moved linearly within said control cable aperture.

6. The convertible laryngoscope according to claim 5, wherein said manual deployment means further includes a first pivot arm pivotally attached to said first pivot point and a second pivot arm pivotally attached to said second pivot point, said first and said second pivot arms sharing an intersecting pivot point.

7. A convertible laryngoscope for aiding in the view of a patient's throat while intubation is being performed, comprising:
   a) a handle
   b) a laryngoscope blade removably detachable from said handle
   c) a mirror integral with and proximate to a terminus of said blade and moveable with respect to said blade, said mirror including manual deployment means for deploying said mirror in a fixed and controlled relationship with said blade, said manual deployment means including a cable and further including a depressible handle integral with said cable for deploying said mirror in a fixed and controlled relationship with said blade; whereby said laryngoscope blade is inserted into the mouth and throat of a patient, and said mirror is deployed through said manual deployment means into a fixed, controlled relationship with said blade such that a line of sight is maintained between a person performing an intubation and the throat of the patient.

8. The convertible laryngoscope according to claim 7, wherein said manual deployment means further includes a first and a second pivot point proximate to, and integral with, said terminus of said laryngoscope blade, and where said first said second pivot points cooperate to extend said mirror when said cable is moved linearly within said control cable aperture.

9. The convertible laryngoscope according to claim 8, wherein said manual deployment means further includes a first pivot arm pivotally attached to said first pivot point and a second pivot arm pivotally attached to said second pivot point, said first and said second pivot arms sharing an intersecting pivot point.

* * * * *